United States Patent

Errico et al.

[11] Patent Number: 5,941,880
[45] Date of Patent: Aug. 24, 1999

[54] COUPLING MEMBER FOR CROSS-LINKING INTERVERTEBRAL CAGE DEVICES

[75] Inventors: Joseph P. Errico, Far Hills; Thomas J. Errico, Summit; James D. Ralph, Oakland, all of N.J.

[73] Assignee: The J7 Summit Medical Group, LLL, Summit, N.J.

[21] Appl. No.: 09/002,536

[22] Filed: Jan. 2, 1998

[51] Int. Cl.⁶ .................................................. A61B 17/70
[52] U.S. Cl. ................................................. 606/61; 623/17
[58] Field of Search ........................... 106/61, 60, 69, 106/70, 71, 72, 73; 623/17

[56] References Cited

U.S. PATENT DOCUMENTS

| | | |
|---|---|---|
| 4,696,290 | 9/1987 | Steffee .................................. 606/61 |
| 5,092,893 | 3/1992 | Smith ................................... 606/61 |
| 5,108,395 | 4/1992 | Laurain ................................. 606/61 |
| 5,549,612 | 8/1996 | Yapp et al. ............................ 606/61 |
| 5,647,872 | 7/1997 | Gilbert et al. ........................ 606/61 |
| 5,676,666 | 10/1997 | Oxland et al. ....................... 606/61 |
| 5,681,311 | 10/1997 | Foley et al. ........................... 606/61 |
| 5,683,391 | 11/1997 | Boyd .................................... 606/61 |

Primary Examiner—Guy V. Tucker
Attorney, Agent, or Firm—Joseph P. Errico, Esq.

[57] ABSTRACT

A cross-linking member for rigidly coupling interbody fusion devices such that they have reduced tendencies to dislocate subsequent to implantation as well as an interbody fusion assembly which includes at least two interbody fusion devices rigidly coupled together by a cross-linking member.

6 Claims, 2 Drawing Sheets

COUPLING MEMBER FOR CROSS-LINKING INTERVERTEBRAL CAGE DEVICES

BACKGROUND OF THE INVENTION

1. Field of the Invention

This invention relates generally to a spinal implant assembly for implantation into the intervertebral space between adjacent vertebral bones to potentiate fusion, and more particularly to a coupling member which is attachable to laterally offset intervertebral cage devices to prevent rolling thereof and to enhance the lateral stability and overall strength thereof

2. Description of the Prior Art

The bones and connective tissue of an adult human spinal column consists of more than 20 discrete bones coupled sequentially to one another by a tri-joint complex which consists of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes which can result in spinal pathologies for which surgical intervention may be necessary. A variety of systems have been disclosed in the art which achieve immobilization and/or fusion of adjacent bones by implanting artificial assemblies in or on the spinal column. The region of the back which needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 1 and 2, in which a perspective view of an intervertebral body cage 10 and a perspective view of an intervertebral spacer device 50 are shown, respectively, a more complete description of these devices of the prior art is herein provided. The cage device 10 generally comprises a tubular metal body 12 having an external surface threading 14. Pairs of these devices are inserted transverse to the axis of the spine, into preformed cylindrical holes at the junction of adjacent vertebral bodies. Two cages 10 are generally inserted side by side with the external threading 14 tapping into the lower surface of the vertebral bone above, and the upper surface of the vertebral bone below. The cages 10 include holes 18 through which the adjacent bones are to grow. Additional material, for example autogenous bone graft materials, may be inserted into the hollow interior 20 of the cage 10 to incite or accelerate the growth of the bone into the cage. End caps (not shown) are often utilized to hold the bone graft material within the cage 10. Intervertebral spacer devices 50 of the type shown in FIG. 2 are similarly positioned, between adjacent vertebral bones, however, they may be solid or hollow, and provide a greater volume of bone graft material to be placed between the two devices 50. More specifically, these intervertebral spacer devices include a solid body 52 having a flat top surface 54 and a flat bottom surface 56. The top and bottom surfaces include serrated ridges 58 which are aligned perpendicular to the axis of the body 52. The sides 60 of the body 52 are concave so that pairs of these devices, when placed side by side, can receive bone graft material between them, thus enhancing the process of bone fusion across the adjacent vertebral bodies.

These cages and intervertebral spacers of the prior art have enjoyed medical success in promoting fusion and grossly approximating proper disc height, however, they do have specific concers regarding their effectiveness. Chief among these concerns is that there will be a tendency for the devices to roll and/or slide. Such undesirable motion by the implant can cause loosening, or worse, complete dislocation from their proper position.

It is, therefore, an object of the present invention to provide an implant which further enhances the stability of cage and/or intervertebral stabilization devices.

It is a further object of the present invention to minimize the risk of dislocation by providing a device which prevents rotational and lateral movement of cage and/or intervertebral stabilization devices.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a cross-linking device for use with interbody fusion implants comprising an elongate coupling body having means for rigidly coupling to prosterior ends of the implants. Additionally, it is an aspect of the present invention to provide a superior interbody fusion implant assembly which includes a cross-linking member. More particularly, with respect to the overall shape of the cross-linking member, the present invention comprises an elongate flat element, having a first hole formed in one elongate end thereof, and a second hole formed in the opposite elongate end thereof It is expected that the holes in the elongate ends of the member will be alignable with axial holes formed in the posterior portions of the interbody fusion elements. These holes provide the means by which the member may be rigidly locked to the interbody fusion elements, such as by screws and/or pins.

In addition, embodiments of the cross-linking member may include a curvature, which is transverse to the elongate axis of the member. This curvature may be included if it can suitably engage a similar curvature of the posterior axial end the conformation of the interbody fusion device. Such mutual curvatures can be utilized to further prevent rotation of the implant relative to the cross-linking member (i.e., in addition to the rigid fixation provided by the screw and/or pin engaging means described above).

Similarly, the cross-linking member may further include a thickened axial portion thereof which mates with, and or engages a nesting recess in the posterior end surface of the implants, to further prevent rotation of the implant relative to the cross-linking member.

As stated previously, it is correspondingly, also an aspect of the present invention to provide a cross-linked interbody fusion device assembly. Such a device comprises at least two interbody fusion implant devices, spaced apart from one another. The implant devices are preferably positioned in parallel, however, it is recognized that surgeon implant technique may not provide accurate alignment, and as a result, the coupling member and means must accomodate slight relative angulations of the implant devices. The assembly further includes the cross-linking member, which must, at minimum, include means for coupling to the posterior axial ends of the at least two implant devices. The mutual conformations of the elongate ends of the cross-linking member (i.e., the positions at which the cross-linking member is secured to the interbody fusion devices) and the at least two implant devices may be of the type described above (or of a similar rotation-inhibiting variety) including at least one anti-rotation engagement means.

The holes formed in the elongate ends of the cross-linking member are aligned with receiving holes in the interbody fusion devices, and are large enough to permit a screw or pin to be used to secure the cross-linking member in place. More particularly, as stated above the means for mechanically coupling the cross-linking member to the interbody fusion implant devices must allow for slight non-perpendicular engagement (if the implants are not placed in parallel to one another, a rigid cross-linking member cannot mutually engage both posterior ends thereof with perfect nesting. The holes, therefore, must be able to receive screws at non-perpendicular relative angles. A variety of such screws are known in the industry, including the polyaxial locking screws set forth in U.S. Pat. No. 5,520,690 et seq., invented by the same inventors of this invention.

During the implantation procedure, the surgeon first removes the degenerated disc material from between the vertebral bodies and then prepares the adjacent exposed bone surfaces for the sequential introduction of the implants. The implant devices are introduced at either lateral side of the intervertebral space, with the posterior axial ends thereof which have the corresponding recess for receiving the coupling means of the cross-linking member facing the surgeon. It is preferred that the implants be as close to parallel as possible. Once properly positioned, the surgeon then places the cross-linking member in position such that it brides the distance between the two implants. At this time, the surgeon may also engage any anti-rotation confirmations of the cross-linking member and/or the implant devices. Once the relative positions of the cross-linking member and the implants has been established, the rigid coupling means (the screws and/or pins) are engaged so that the cross-linking member, and by association, the two implants, are rigidly fixed together. Subsequent undesirable rotation of either implant is thereby reduced considerably, thus greatly enhancing the potential for one mode of failure of these interbody fusion implant devices.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
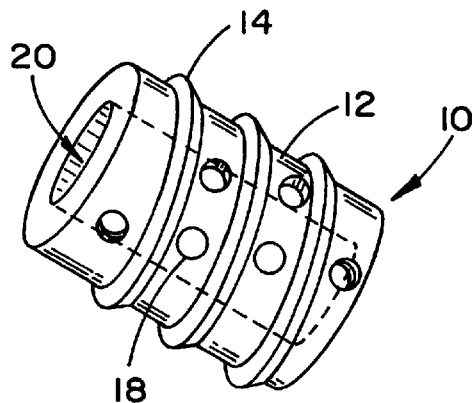
FIG. 1 is a perspective view of a cage-type interbody fusion device of the prior art.
Figure 2:
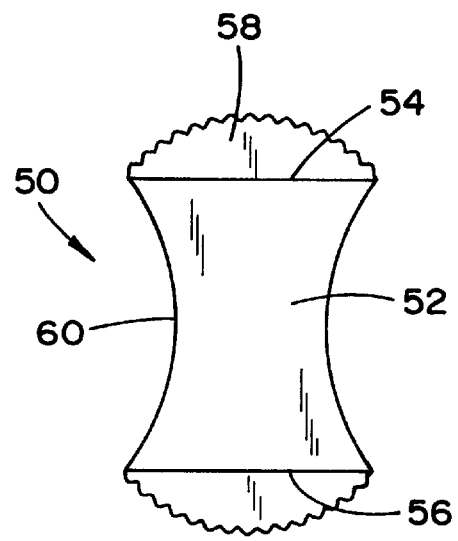
FIG. 2 is aperspective view of an intervertebral spacer-type interbody fusion device of the prior art.
Figure 3:
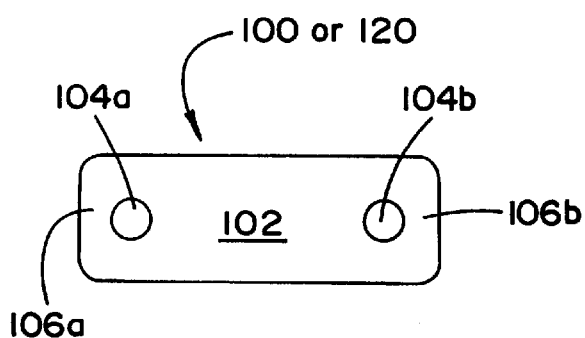
FIG. 3 is a top view of a one embodiment of the present invention.
Figure 4:
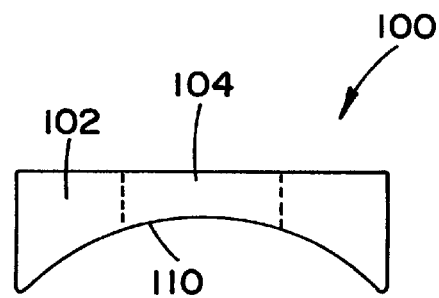
FIG. 4 is an end view of the embodiment of the present invention illustrated in FIG. 3.
Figure 5:
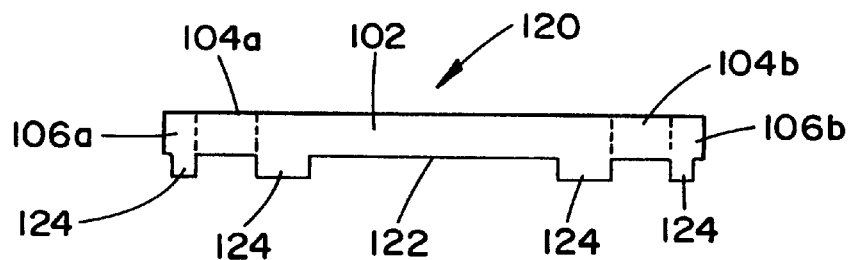
FIG. 5 is an end view of an alternative embodiment of the present invention having the same top conformation as shown in FIG. 3.

Referring now to FIGS. 3, 4, and 5, two alternative embodiments of the present invention is provided in top and side perspective views, respectively. Each embodiment shares a similar visual appearance as illustrated from the top view, however, the undersurface conformations of each are distinguishable, as shown in FIGS. 4 and 5. In both embodiments 100 or 120, however, the present invention comprises an elongate coupling body 102 which is ideally constructed of a metal having both tissue compatibility with the patient and electrochemical compatibility with the implants which it is cross-linking (this being important lest a voltage be developed and potential electrically driven corrosion occur). More particularly, with respect to the overall shape of this cross-linking member 100 or 120, the present invention comprises an elongate member 102 having a first hole 104a formed in one elongate end 106a thereof, and a second hole 104b formed in the opposite elongate end 106b thereof. It is expected that the holes 104a, 104b in the elongate ends 106a, 106b of the member will be alignable with axial holes formed in the posterior portions of the interbody fusion elements (see FIGS. 6 and 7). These holes 104a, 104b provide the means by which the member 100 or 120 may be rigidly locked to the 1S interbody fusion elements, such as by screws and/or pins.

Referring now, specifically, to FIG. 4, this first embodiment of the cross-linking member 100 further includes an axial curvature, which is transverse to the elongate axis of the member. More particularly, this curvature renders the surface 110 of the member 100 which directly contacts the intervertebral fusion elements to be concave. This curvature is included so that the member may nest on the posterior axial of the interbody fusion device, provided it also includes a similar curvature (see FIG. 6). Such mutual curvatures are utilized to further prevent rotation of the implants relative to the cross-linking member 100 by an interference fit against the fusion element.

Figure 7:
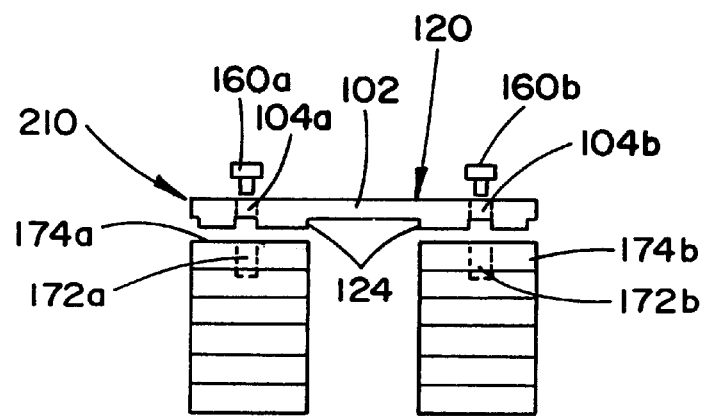
FIG. 7 is a perspective view of an assembly embodiment of the present invention utilizing the embodiment of the cross-linking member illustrated in FIG. 5.

Alternatively, FIG. 5 illustrates another possible contact surface conformation 122 which engages the posterior end of the interbody fusion device (see FIG. 7). In this embodiment 120, the contact surface includes linearly aligned axial (relative to the elongate body 102) ridges 124 which mate with, and or engage corresponding recessed conformations of the posterior ends of the interbody fusion devices. Similarly, this correspondence between the contact surface conformation and the posterior ends of the implants is designed to further prevent rotation of the implants relative to the cross-linking member and relative to each other and the patient.

Figure 6:
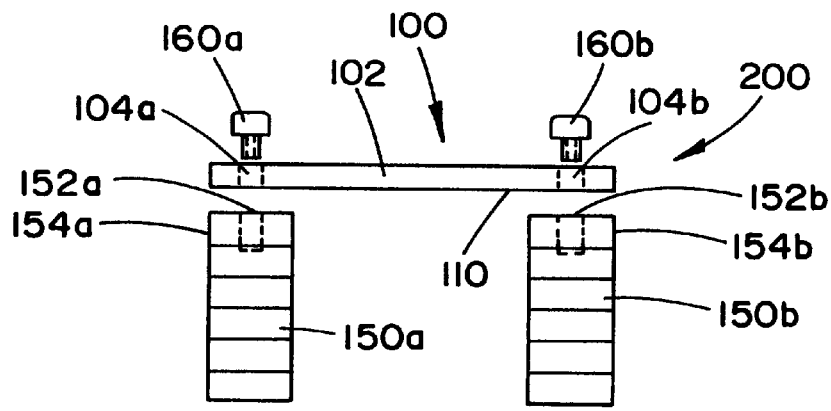
FIG. 6 is a perspective view of an assembly embodiment of the present invention utilizing the embodiment of the cross-linking member illustrated in FIG. 4.

Referring now to FIGS. 6 and 7, in which perspective drawings of the cross-linking member 100 and 120, respectively, are shown in combination with interbody fusion devices 150a and 150b, another aspect of the present invention is provided comprising a full implant assembly. More particularly, the full spinal implant assembly 200, which is an aspect of this present invention comprises a cross-linking member 100 (as set forth hereinabove with respect to FIGS. 3 and 4), a pair of interbody fusion devices 150a, 150b, and a pair of set screws. The surgical procedure for implanting this assembly begins with the positioning of the interbody fusion devices 150a, 150b laterally within the intervertebral space. The devices 150a, 150b include posterior ends 154a, 154b, respectively, which are convexly contoured to nest within the concave conformation of the contact surface 110 of the cross-linking member 100.

Once the devices have been properly positioned, with the posterior ends 154a, 154b facing in the same direction, the cross-linking member 100 may be introduced such that the holes 104a, 104b are aligned with threaded holes 152a, 152b in the posterior ends 154a, 154b of the interbody devices 150a, 150b respectively. Set screws 160a and 160b are each inserted into the corresponding holes 104a, 104b and 152a, 152b and tightened so that the cross-linking member 100 is rigidly fixed to each implant device, and they are simultaneously affixed to one another.

Referring now to FIG. 7, the alternative implant assembly 210 utilizing the alternative cross-linking member 120 is shown in a perspective view. This second implant assembly is similar to the first insofar as it includes a pair of interbody fusion devices 170a, 170b having posterior ends 174a, 174b, respectively, and threaded holes 172a, 172b(for receiving threaded set screws 160a,160b). The posterior ends 174a, 174b of these implant devices, however, each include a linear recess disposed across the posterior end thereof This linear recess corresponds with the linear ridges 124 disposed on the contact surface 122 of the cross-linking member. The assembly is built within the patient a the manner very much similar to that described above for the first assembly 200 set forth above with respect to FIG. 6, but for the fitting of the ridges 124 into the recesses of the posterior ends 174a,174b.

While there has been described and illustrated implantation devices for stabilizing and immobilizing regions of the spine by inserting a pair of interbody fusion devices into the intervertebral space between adjacent vertebral bodies and aligning and rigidly coupling those interbody fusion devices with a cross-linking member, it will be apparent to those skilled in the art that variations and modifications are possible without deviating from the broad spirit and principle of the present invention which shall be limited solely by the scope of the claims appended hereto.

We claim:

1. An interbody fusion assembly comprising:
    at least two interbody fusion implant devices having first and second axial ends, said first axial ends of each including an axial hole therein which hole is threaded and an axially curvate engaging contour;
    a flat elongate member having at least two corresponding through holes for coupling said member to corresponding interbody fusion implant devices at said through holes, and a surface thereof having a corresponding nesting curvate engaging contour suited to engage said engaging contour of said at least two interbody fusion implant devices; and
    means for coupling said member to said at least two interbody fusion devices at said through holes.

2. The interbody fusion assembly as set forth in claim 1, wherein said means for coupling said member to said at least two interbody fusion devices at said trough holes comprises at least two corresponding set screws.

3. The interbody fusion assembly as set forth in claim 1, wherein said axially curvate contour of said coupling member is axially concave.

4. The interbody fusion assembly as set forth in claim 1, wherein said axially curvate contour of said coupling member is axially convex.

5. The interbody fusion assembly as set forth in claim 1, wherein said engaging contour of said coupling member comprises axially aligned ridges and the engaging contour of said first ends of said at least two interbody fusion devices comprises a linear recess formed in said first ends contour.

6. The interbody fusion assembly as set forth in claim 1, wherein said means for rigidly coupling said coupling member to said at least two interbody fusion devices at said through holes comprises at least two corresponding set screws.

* * * * *